United States Patent [19]

Engle

[11] 4,361,043

[45] Nov. 30, 1982

[54] REFERENCE VOLTAGE GENERATION MEANS FOR CONTROLLING A DISPLAY

[75] Inventor: Gary L. Engle, Fair Oaks, Calif.

[73] Assignee: General Electric Company, Rancho Cordova, Calif.

[21] Appl. No.: 203,656

[22] Filed: Nov. 3, 1980

[51] Int. Cl.³ ............................................. G01N 29/00
[52] U.S. Cl. ....................................... 73/620; 128/660
[58] Field of Search ................. 73/620, 618, 619, 633, 73/634, 607; 367/7; 358/112; 128/660

[56] References Cited

U.S. PATENT DOCUMENTS

| | | | |
|---|---|---|---|
| 4,172,386 | 10/1979 | Cribbs et al. | 73/618 |
| 4,204,433 | 5/1980 | Cribbs et al. | 73/620 |
| 4,206,654 | 6/1980 | Keller et al. | 73/620 |

Primary Examiner—Stephen A. Kreitman
Attorney, Agent, or Firm—Flehr, Hohbach, Test, Albritton & Herbert

[57] ABSTRACT

A position reference voltage for controlling the electron beam of a display in an ultrasonic scanning system includes circuitry for receiving a position voltage from a scanner in the system, and a voltage from a variable voltage source. When the variable voltage exceeds the position voltage the variable voltage is locked whereby a new position voltage for the display is derived from the sum of the locked voltages and the scanner position voltage. The variable voltage source includes a digital counter and a digital to analog converter. A comparator compares the sum of the variable voltage and the scanner position voltage, with a reference potential and a flip-flop responds to the comparator to disable the counter when the summed voltages exceed the reference potential.

9 Claims, 4 Drawing Figures

REFERENCE VOLTAGE GENERATION MEANS FOR CONTROLLING A DISPLAY

This invention relates generally to scanning systems such as ultrasound scanners as used for medical diagnostic purposes, and more particularly the invention relates to displays for use in such systems.

Ultrasonic diagnostic systems are known and commercially available for diagnostic purposes. See for example U.S. Pat. No. 4,172,386 for "Video A Trace Display System For Ultrasonic Diagnostic System" and U.S. Pat. No. 4,204,433 for "Computerized Ultrasonic Scanner With Technique Select." The commercially available Datason ultrasonic system of General Electric Company provides both real time and static images on a television display.

Briefly, such systems utilize sound transducers to transmit ultrasonic (e.g. on the order of several megahertz) waves into a patient and to receive echo signals. The transducer is attached to a plurality of hinged arms for movement in a single plane, and potentiometers associated with the hinged arms produce signals which identify the transducer position. The echo signals are applied to a time gain compensated amplifier to adjust the echo signals for attenuation in passing through the patient. The adjusted signals then pass through analog to digital conversion and video processing circuitry and thence to scan converter circuitry for display formatting. The display comprises a plurality of pixels in horizontal rows and vertical columns with each pixel having a brightness level in response to the input signal. Conventionally, the brightness is defined by a 32 level Gray scale, hence the pixel brightness level requires a 5 bit digital code. The pixel brightness code is stored in a random access memory with the memory periodically updated in response to video signals produced from the ultrasonic scanning.

The pixels displayed on the monitor correspond to positions in the plane of motion of the scanner relative to a reference position of the scanner. As the scanner moves from the plane reference position, increasing voltages are generated by the potentiometers which identify the scan position. However, in the ultrasound system any point in the scan plane can be established as a reference point for display, such as when an internal organ is to be displayed. Heretofore, in generating a voltage for a new reference point, the voltages from the potentiometers have been readjusted to give a reference or zero voltage at the new reference point.

An object of the present invention is an improved method of obtaining reference voltages for controlling a display in a scanning system.

Another object of the invention is reference voltage generation means having greater accuracy and stability.

A feature of the invention is the use of a digital counter and a digital to analog converter to provide an offset voltage in establishing a new reference voltage for controlling the display.

Briefly, in accordance with the invention means for establishing a new reference position signal for controlling a display relative to a desired reference position in a scanner plane of motion comprises voltage means for generating a variable voltage, comparator means for receiving and comparing the variable voltage and the position voltage from the scanner, and means responsive to the comparator means for holding the voltage means at a fixed voltage level when the comparator means indicates that the variable voltage exceeds the position voltage. The new position signals for controlling the display is then derived from the sum of the scanner position voltage and the fixed voltage level.

To provide improved accuracy and stability, the variable voltage means comprises a digital counter and a digital to analog converter responsive to count from the counter. In establishing the new reference position voltage, the counter provides an increasing count to the converter whereby the converter generates a negative voltage which decreases in magnitude in response to increasing count from the counter.

The means responsive to the comparator means for holding the variable voltage means at a fixed voltage level preferably includes a flip-flop circuit which responds to the output of comparator and changes state when the variable voltage exceeds the position voltage. The output of the flip-flop then disables the digital counter and fixes the count within the counter.

The invention and objects and features thereof will be more readily apparent from the following detailed description and appended claims when taken with the drawing, in which:

Figure 1:
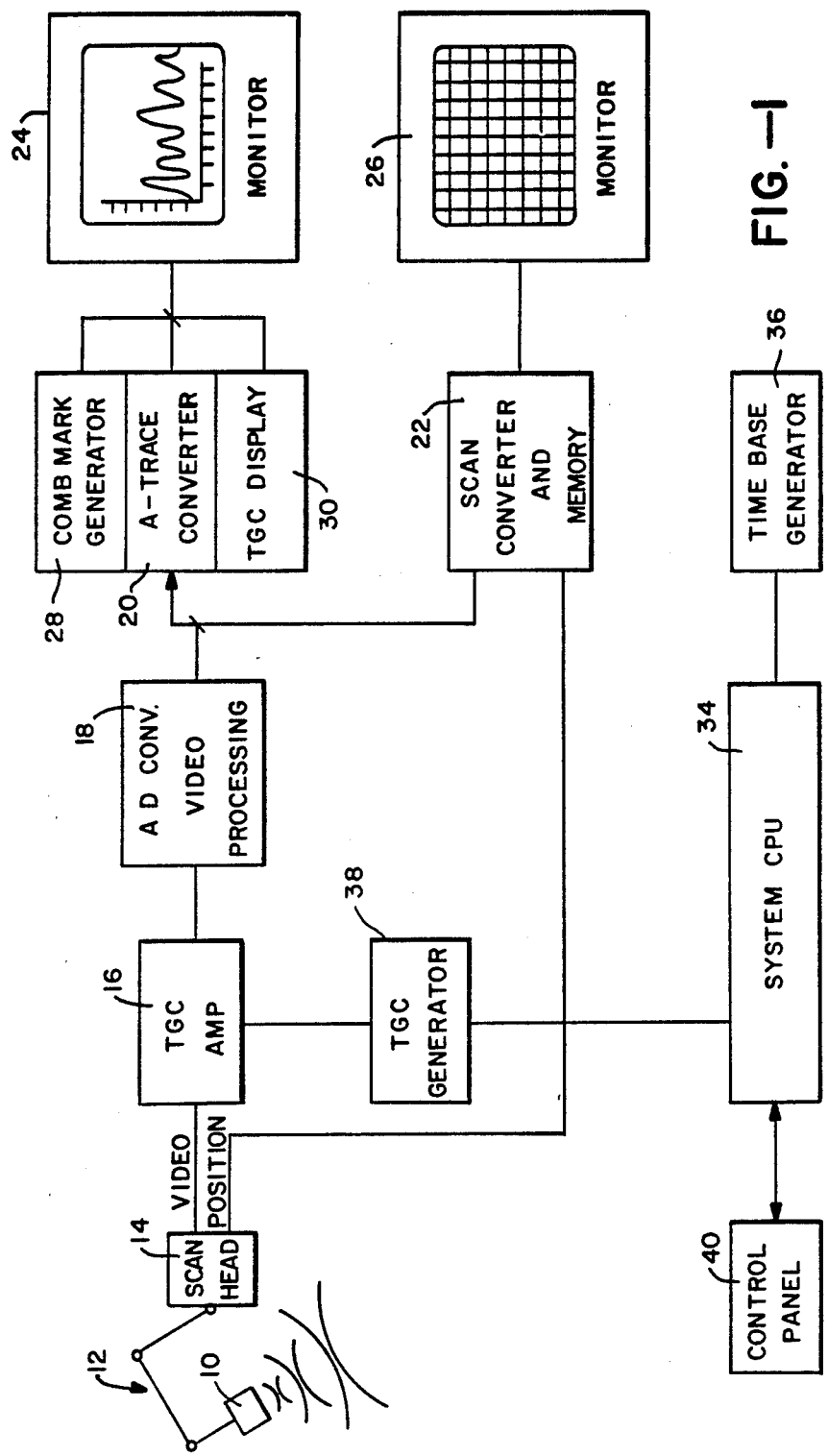
FIG. 1 is a functional block diagram of a conventional ultrasonic scanner system.

Referring now to the drawings, FIG. 1 is a functional block diagram of an ultrasonic scanner. The system includes a transducer 10 mounted on a hinged arm system shown generally at 12 whereby transducer 10 can move freely in a single plane. Potentiometers in scan head 14 and associated with the arms of the system generate signals indicative of the X and Y position of the scanner 10 in the plane of motion.

Scanner 10 transmits ultrasonic signals (e.g. on the order of 5 megahertz) and generates electrical signals in response to reflections of the transmitted ultrasonic signals. The generated signals are attenuated in time due to attenuation of the ultrasonic signal in passing through a patient.

The attenuated video signal is then applied to a time gain compensated amplifier 16, and the amplifier signal is then applied to analog to digital conversion and video processing circuitry 18. The output of circuitry 18 is then applied to A trace converter circuitry 20 and to scan converter and memory circuitry 22 which generate the signals for controlling television monitors 24 and 26, respectively.

The A trace converter generates a signal for real time display of the amplitude of each reflected ultrasonic wave. The A trace data applied to monitor 24 identifies a horizontal position on the monitor (e.g. 1,000 positions) and an amplitude or vertical position associated with each X position. This data controls an intensity of the electron beam in the display during raster scanning of the beam. Scale markings for the displayed A trace are generated by comb mark generator 28, and a time gain compensation curve is provided by generator 30.

A section view of the patient is displayed on monitor 26 in response to the scan converter and memory 22. The signal from circuitry 18 is converted for storage in a 512×512 memory matrix with each point in the matrix accommodating a 5 bit brightness code. The matrix corresponds to the pixels on the display of monitor 26 with the brightness code being indicative of the Grey scale for the pixels.

System control is provided by a central processing unit 34 which also drives a time base generator 36 which generates the timing signals for the system. A time gain compensation (TGC) control generator 38 generates the control signal for amplifier 16 and a control panel 40 is provided for manual control of the system through the central processing unit.

Figure 2:
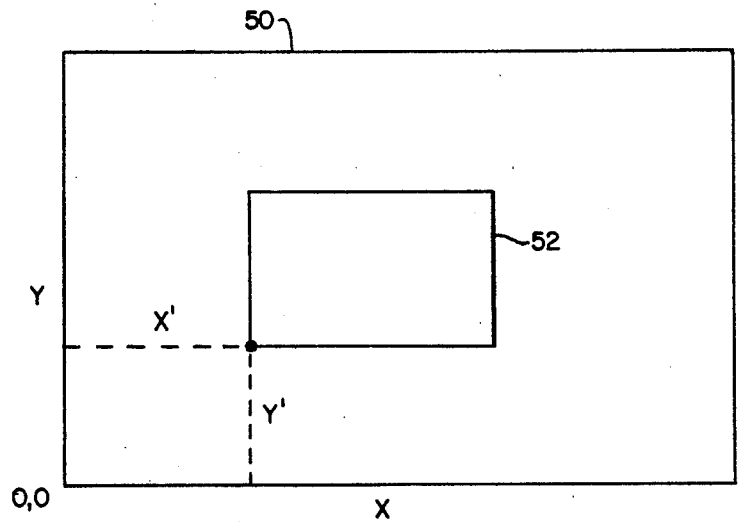
FIG. 2 is a representation of a scan plane and reference positions therein.

The pixels in monitor 26 correspond in location to the scan area of the transducer 10. FIG. 2 is a representation of the field of scan 50 of the scanner 10 with the field of scan conventionally represented by X and Y coordinates. Normally, a reference position (0,0) is established for the scanner at which point the potentiometers associated therewith produce a zero voltage signal indicative of the X and Y positions. As the scanner moves from the reference point increasing positive voltages are generated by the potentiometers with the voltages indicative of the new X and Y positions of the scanner. The X and Y positions of the transducer along with the inclination of the scanner are used in the scanned converter to generate vectors comprising a plurality of addressable pixels whereby video signals can be associated with the pixels for the indicating brightness.

Often it is desired to change the reference point in the field of scan for display purposes whereby a smaller area 52 can be enlarged for display on the monitor 26. In so identifying the smaller area 52 a new reference point defined by the coordinates X', Y' must be established for controlling the vector generation. Heretofore, this has been established by moving the scanner to the desired new reference point and adjusting the voltage from the potentiometers to give zero voltage outputs for the X' position and the Y' position. This is accomplished by adjusting the voltage range of the potentiometers from a zero voltage level to a negative voltage level at the (0,0) position defined by the X' and Y' offsets. However, by so adjusting the potentiometer voltages the accuracy and stability of the displayed image is limited.

In accordance with the present invention a new reference position voltage is established for controlling a display by moving the scanner to the new reference position, comparing the scanner position voltage with a variable voltage, and locking the variable voltage just when it exceeds the position voltage. A digital counter and digital to analog converter interconnected with the counter are employed to provide the variable voltage. Improved accuracy and stability is realized by establishing a requisite count in the counter for controlling the digital to analog converter at the new reference voltage level.

Figure 3:
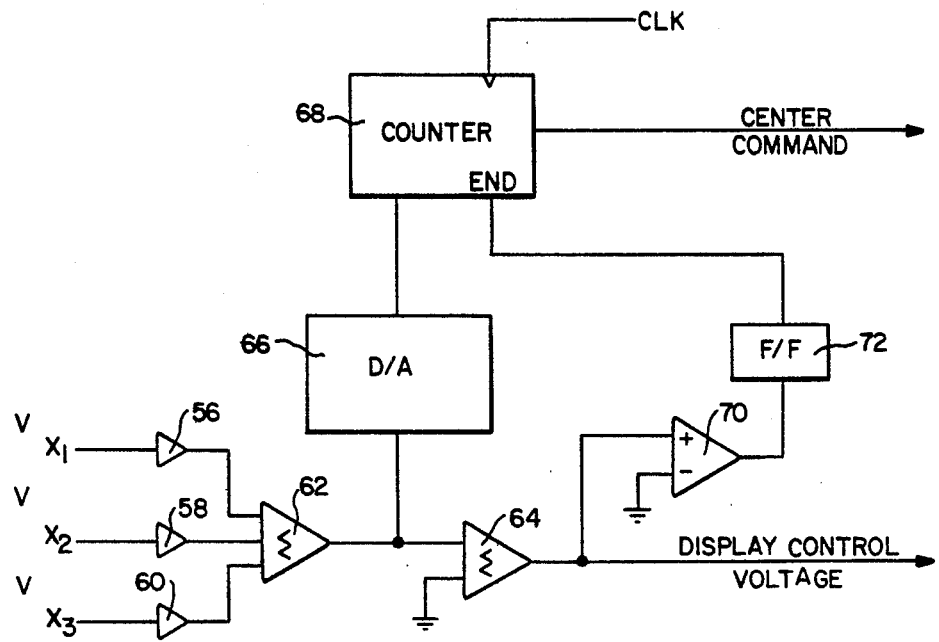
FIG. 3 is a functional block diagram of apparatus for generating a reference position signal for a display in accordance with one embodiment of the invention.

FIG. 3 is a block diagram of one embodiment of the apparatus in accordance with the invention. Typically, three voltages, $V_{X1}$, $V_{X2}$, and $V_{X3}$ are associated with three arms in the linkage to indicate the X coordinate of the scanner. Similarly, three voltages are provided for indicating the Y position of the scanner. The three voltages indicative of the X position are applied through buffers 56, 58 and 60 to a summing amplifier 62. The output of summing amplifier 62 is then applied to a second summing amplifier 64 along with the output from a digital to analog converter 66. The digital to analog converter 66 is interconnected with a counter 68 and responds to the digital count to provide a negative voltage which decreases in magnitude in response to increasing count in counter 68.

Connected to the output of amplifier 64 is a comparator 70 which compares the output voltage of amplifier 64 with ground potential. The output of amplifier 70 is connected to an input of flip-flop 72 whereby a positive voltage from comparator 70 triggers flip-flop 72. The output of flip-flop 72 is connected with the enable input to counter 68 whereby a change of state of flip-flop 72 disables the counter 68 and maintains the count of the counter therein.

In establishing the new reference voltage the transducer is moved to the desired reference position, and a center command from the front panel of the system initiates counter 68.

The increasing count from counter 68 is applied to the converter 66 which generates a negative voltage having decreasing magnitude in response to increasing count. The negative voltage from converter 68 is summed with the positive position voltage from amplifier 62 in the amplifier 64, and the summed voltage is applied to the comparator 70. When the summed voltage at the output of amplifier 64 exceeds zero level indicative of the new reference position voltage, comparator 70 generates a positive output which triggers flip flop 72 and disables counter 68. Thus, the digital to analog converter 66 maintains the requisite voltage to offset the position voltage from the scanner to provide a new zero voltage reference signal. The output voltage from amplifier 64 is then applied as the display position control voltage.

Figure 4:
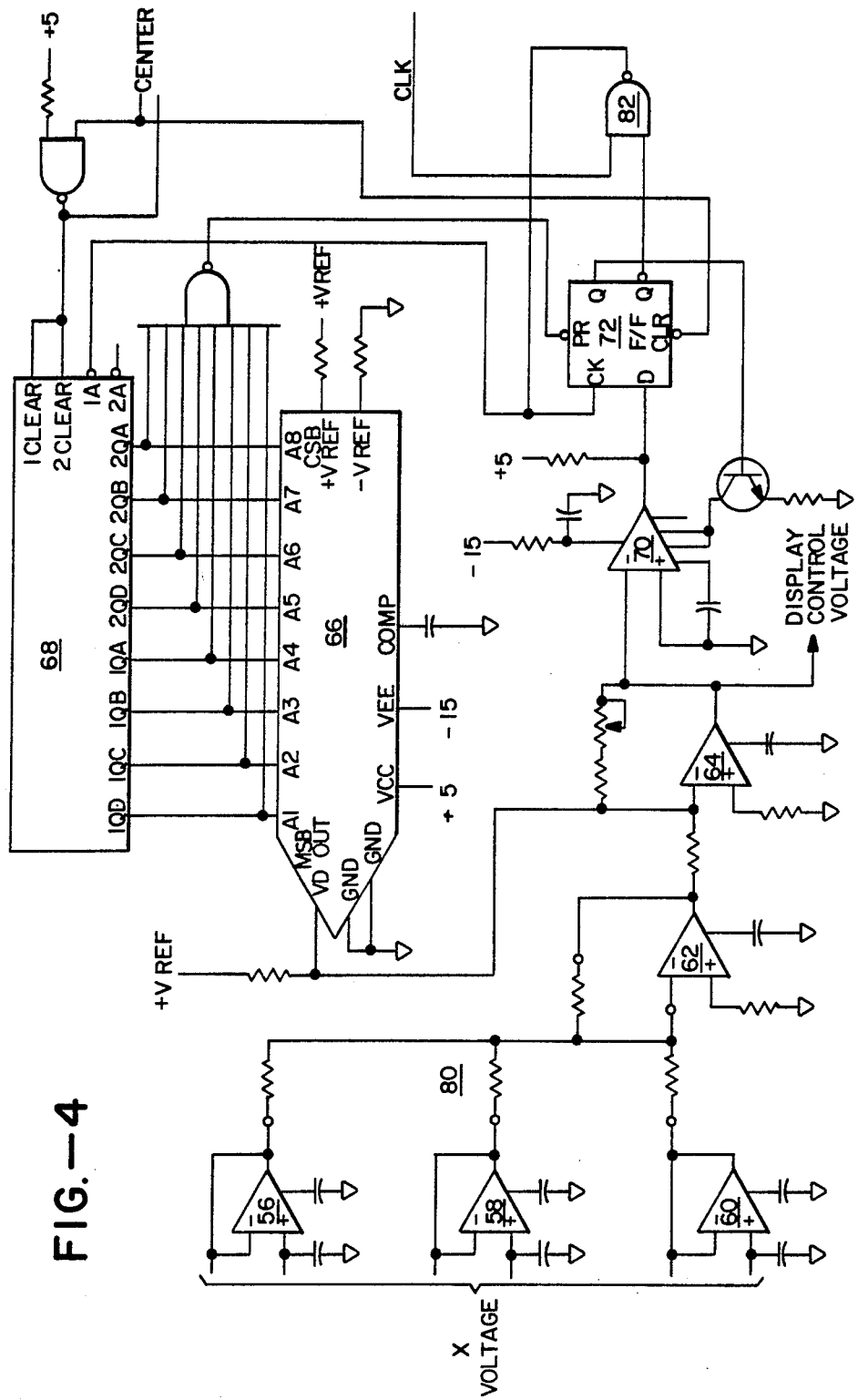
FIG. 4 is a more detailed block diagram of the circuitry of FIG. 3.

FIG. 4 is a schematic of the circuitry of FIG. 3 as used with the Datason system. Like elements in the two figures have the same reference numerals, and the commercial components are indicated in parentheses. The three voltages indicative of the X position of the scanner are applied through the buffers 56, 58, and 60 (National LM 308), and the outputs of the buffers are then applied through a resistive network 80 which weighs the signals in accordance with the varying arm lengths of the linkages associated therewith. The weighted signals are then applied to the summing amplifier 62 (National LM 308) with the output of summing amplifier 62 applied to an input of summing amplifier 64 along with the output from the digital to analog converter 66 (AMD DAC 0808). The output of amplifier 64 provides the display control voltage and is also connected to the comparator 70 (National LM 311) with the output of amplifier 70 connected to an input of flip-flop 72 (National 74LS74).

The $\bar{Q}$ output of flip-flop 72 is connected to NAND gate 82 along with the clock signal (one Mhz in the Datason system), and the output of gate 82 is interconnected to disable the counter 68 (National 74LS393) upon the output of NAND gate going negative. NAND gate 84 is connected to the outputs of the counter 68 to trigger flip-flop 72 when the counter reaches full count. Thus, an overflow of the counter is prevented. The center command signals from the front panel are applied to counter 68 to initiate the new reference or center location operation.

Apparatus in accordance with the present invention provides an accurate and stable position control signal for displaying an image in a scanning system. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. In a system in which a display is responsive to signals from a scanner including position voltages from said scanner relative to a reference scanner position and reference voltage, means for establishing a new reference position signal for said display when said scanner is at a desired new reference position comprising voltage means for generating a variable voltage, comparator means for receiving and comparing said variable voltage and said position voltage from said scanner, and, means responsive to said comparator means for holding said voltage means at a fixed voltage level when said comparator means indicates that said variable voltage exceeds said position voltage.

2. Means for establishing a new reference position signal as defined by claim 1 wherein said position signal for said display is derived from the sum of said variable voltage and said position voltage.

3. Means for establishing a new reference position signal as defined by claim 2 wherein said voltage means comprises a digital counter and a digital to analog converter responsive to count from said counter.

4. Means for establishing a new reference position signal as defined by claim 3 wherein said means responsive to said comparator means comprises a flip-flop circuit which changes state in response to said comparator indicating that said variable voltage exceeds said position voltage, said flip-flop interconnected with said counter to disable said counter when said flip-flop changes state.

5. In an ultrasonic scanner system and the like in which the position of a scanner on a display is defined by X and Y coordinates expressed in voltage levels relative to a reference voltage level at a reference scanner position, apparatus responsive to position voltages from the scanner for establishing a new reference point for controlling the display comprising first means for providing a voltage in response to voltages from said scanner when said scanner is moved to a desired reference point, counter means, digital to analog converter means interconnected with said counter means for generating a variable voltage in response to count from said counter means, comparator means for receiving and comparing said variable voltage from said digital to analog converter and said voltage from said first means, and means connected with said comparator means for stopping a count in said counter means when said variable voltage exceeds said voltage from said first means whereby a voltage from said comparator means establishes a new position voltage for controlling said display.

6. Apparatus as defined by claim 5 wherein said first means comprises summing means for X position voltages from said scanner.

7. Apparatus as defined by claim 5 wherein said first means comprises summing means for Y position voltages from said scanner.

8. Apparatus as defined by claim 5, 6 or 7 wherein said comparator means comprises summing means for summing said variable voltage and said voltage from said first means and a comparator for comparing voltage from said summing means and a reference voltage level.

9. Apparatus as defined by claim 8 wherein said voltage from said first means is a positive voltage, said variable voltage is a negative voltage having decreasing magnitude, and said means for stopping a count in said counter means comprises a flip-flop responsive to said comparator and interconnected with said counter to disable said counter.

* * * * *